Figure 1:
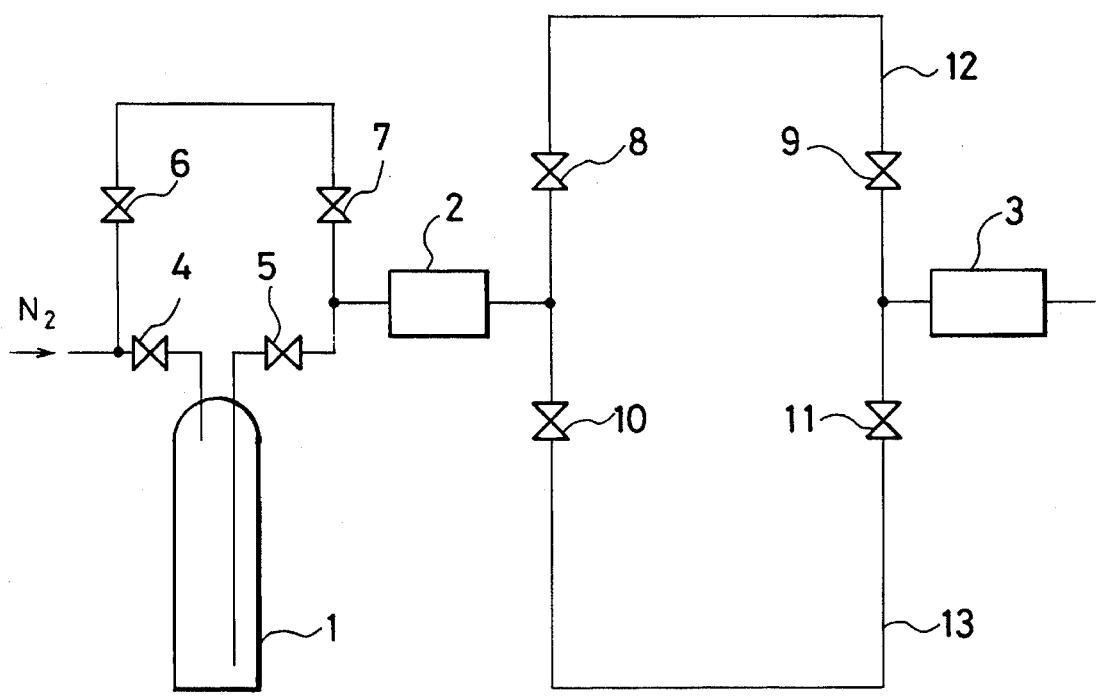

United States Patent
Ohmi et al.

Patent Number: 5,504,009
Date of Patent: Apr. 2, 1996

[54] METHOD OF AND DEVICE FOR MEASURING WATER CONTENT

[75] Inventors: Tadahiro Ohmi, 1-17-301, Ko-megabukuro 2-chome, Aoba-ku, Sendai-shi, Miyagi-ken 980; Jun Takano, Miyagi, both of Japan

[73] Assignee: Tadahiro Ohmi, Sendai, Japan

[21] Appl. No.: 182,109

[22] Filed: Jan. 14, 1994

[30] Foreign Application Priority Data

Jul. 16, 1991 [JP] Japan ................................. 3-201422

[51] Int. Cl.$^6$ .................................................. G01N 33/18
[52] U.S. Cl. .................... 436/39; 436/149; 422/82.02
[58] Field of Search .................. 436/39, 149; 422/82.02; 252/194, 964; 340/604, 605

[56] References Cited

U.S. PATENT DOCUMENTS

| | | | |
|---|---|---|---|
| 3,222,292 | 12/1965 | Nadolski | 436/39 |
| 3,243,674 | 3/1966 | Ebert | 436/39 |
| 3,354,057 | 11/1967 | Klingelhoeffer | 436/39 |
| 4,975,249 | 12/1990 | Elliot | 422/83 |

FOREIGN PATENT DOCUMENTS

| | | |
|---|---|---|
| 54-143197 | 11/1979 | Japan . |
| 63-182565 | 7/1988 | Japan . |
| 2164402 | 2/1990 | Japan . |
| 3-2660 | 1/1991 | Japan . |
| 8600711 | 1/1986 | WIPO . |
| 9304366 | 4/1993 | WIPO . |

OTHER PUBLICATIONS

"Trace Moisture Analysis in Specialty Gases", Ohmi et al, J. Electrochem. Soc. vol. 139, No. 9 Sep. 1992.
"Conductivity and Dissociation Eq. of Extremely Amhydrous Hydrogen Fluoride", Miki et al, Electrochem Soc. vol. 137, No. 3 Mar. 1990.
"New Techniques for Measurement in Said Surface", Ohmi et al Rev. Sci Instrum. 94(9) Sep. 1993 [Does Not Qualify as Prior Art].

Primary Examiner—Timothy M. McMahon
Assistant Examiner—N. Bhat
Attorney, Agent, or Firm—Baker & Daniels

[57] ABSTRACT

This invention consists in a device consisting of a vessel (1) containing chemical solution soluble in water, a sample room or sample itself (13), and electric conduction meter (3); and a method in which the chemical solution is brought into contact with the sample so as to absorb water adsorbed to the surface of the sample and then electric conductivity of the chemical solution is measured. By means of such a structure as above, water content having been adsorbed by the sample can be measured with high precision in a short, period of time.

2 Claims, 3 Drawing Sheets

METHOD OF AND DEVICE FOR MEASURING WATER CONTENT

TECHNICAL FIELD

The present invention relates to a method and device for measuring water content. For example, the present invention is preferably employed in the determination of the water content adsorbed to the surface of various materials, such as the determination of the water content adsorbed to a thin film surface such as a silicon film or a silicon oxide film or the like formed on the inner surface of a highly clean electropolished pipe, the determination of the water content adsorbed to a metal surface, or the like; furthermore, the present invention relates to a method and device for measuring water content which is capable of determining the water content adsorbed to various types of wafer surfaces in production processes of semiconductors and water content adsorbed to inner surfaces of semiconductor manufacturing apparatuses.

BACKGROUND ART

In order to achieve a shift to ultra LSI and to attain higher performance, an atmosphere having greater and greater cleanliness is required for the formation and processing of the elements, and technology for the production of ultrahigh vacuums, ultraclean low pressure atmospheres, ultrahigh purity gas atmospheres, and supply systems has become more important.

Such atmospheres are contaminated by leaks from the outside of the apparatus or the gas piping system, or by desorption of impurities adsorbed to the inner surface thereof. Among these impurities, water molecules adsorbed by the inner surface of the apparatus or the gas piping system, in particular, desorb during manufacturing processes such as, for example, thin film formation or processing, and the contamination of the atmosphere as a result of the desorption of these adsorbed molecules creates a problem in, that it tends to cause a worsening of the characteristics of the elements or of the precision of the processing.

Accordingly, it is necessary to construct such semiconductor manufacturing apparatuses using material having a small adsorbed water content, and from which the adsorbed water desorbs easily and within a short period of time; for this reason, surface treatment, such as planarization treatment, post-oxidation passivation treatment, fluoridation passivation treatment, and the like, is carried out on the surface of the structural material.

In order to produce a highly clean atmosphere containing no moisture, it is necessary to develop materials having little adsorbed water and to develop materials from which adsorbed water desorbs quickly, and methods of evaluation by which the amount of water adsorbed by a wafer or the like can be accurately measured after various types of manufacturing processes.

Conventionally, in the case in which amounts of water adsorbed by piping or the like were measured, methods were employed in which a gas of high purity (for example, Ar gas having a water content of less than 50 ppt) was caused to flow through piping as a carrier gas while subjecting the piping to baking, and the desorbing water content was analyzed by means of an atmospheric pressure ionization mass spectrometer (APIMS) or by the Karl Fisher method.

However, in the method in which an APIMS was employed, a number of hours were required for the water molecules adsorbed by the surface of the sample to completely desorb and for the water content concentration in the carrier gas to return to its original value, so that high speed measurement was not possible, and furthermore, there was an upper limit to the measurement of high moisture concentrations. Furthermore, in the Karl Fisher method, it was unclear whether the water molecules contained in the carrier gas were completely absorbed into the solvent, and furthermore, there was a lower limit to the measurement of low moisture concentrations, so that a method having a high degree of reliability was not available. In this situation, there was a strong demand for a method for measuring adsorbed water content which had high reliability and which was capable of rapid measurement.

The above discussion centered on the field of semiconductor manufacturing technology; however, this is not limited to the semiconductor field, but rather, in the manufacture of magnetic discs, laser discs, and micro devices such as liquid crystals and EL flat plate displays, and the like, as well, in order to attain high performance manufacturing processes, a method for the measurement of water content adsorbed by solid surfaces is very important, as remaining adsorbed water content presents the greatest obstacle.

The present invention has as an object thereof to provide a measurement method and a measuring device for measuring water content, which is capable of measuring water content adsorbed by various samples, with high precision and in a short period of time.

DISCLOSURE OF THE INVENTION

A first feature of the present invention resides in a measurement method for water content, characterized in that a chemical solution possessing solubility in water, i.e. a hydrophilic solution, is brought into contact with a sample, and thereby the water content adsorbed by the surface of the sample is absorbed into the chemical solution, and subsequently, the electric conductivity of the chemical solution is measured.

A second feature resides in a device for measuring water content, characterized in that a storage vessel for storing a chemical solution possessing solubility in water, a sample room or a sample itself, and an electric conduction meter are provided, and furthermore, a mechanism for supplying chemical solution from the storage vessel to the sample room or the sample itself while controlling the flow rate of the chemical solution within the storage vessel, and a mechanism for sending chemical solution from the sample room or the sample itself to the electric conduction meter, are provided.

FUNCTION

When a chemical solution having a large mutual interaction with water, such as anhydrous hydrogen fluoride, is brought into contact with a solid sample, the water molecules adsorbed by the solid surface are quickly absorbed into the chemical solution. The water molecules absorbed into the chemical solution dissociate into ions in the chemical solution, and as a result, the electric conductivity varies in accordance with the amount of water content. Accordingly, by measuring the electric conductivity of the chemical solution, it is possible to measure the water content adsorbed by the solid surface.

Furthermore, by using a chemical solution having a large mutual interaction with water, such as anhydrous hydrogen fluoride, the water is easily dissolved in the chemical solution irrespective of the state of the surface adsorbing the water, so that it is possible to conduct the measurement of the adsorbed water content in a short period of time.

EMBODIMENT EXAMPLES

A structural example of the present invention is shown in FIG. 1; using this FIGURE, the embodiment examples of the present invention will be explained.

In the FIGURE, reference 1 indicates a chemical solution storage vessel, reference 2 indicates a chemical solution flow rate control mechanism, reference 3 indicates a leak-tight electric conduction meter, and reference 12 indicates a reference pipe for maintaining the interior portion of the sensor cell of the electric conduction meter in an ultraclean state. Reference 13 indicates a sample pipe which is produced with a variety of interior surfaces and which adsorbs water.

Valves 4 and 5 are opened, a highly pure inert gas (for example, $N_2$, Ar, or the like) is introduced into chemical solution storage vessel 1, pressure is applied, and chemical solution is supplied from vessel 1 to the piping side. The flow rate of the chemical solution flowing through the piping is controlled at a fixed flow rate by the flow rate control mechanism 2. First, valves 8 and 9 are opened, and valves 10 and 11 are closed, and thereby, the chemical solution is sent via reference pipe 12 to electric conductivity meter 3, and here, the electric conductivity of the chemical solution is measured. When the electric conductivity reaches a constant value valves 8 and 9 are closed, and valves 10 and 11 are opened, and chemical solution is introduced into sample pipe 13 and the adsorbed water content of the sample pipe is dissolved, and the chemical solution is then sent to electric conduction meter 3.

Figure 2:
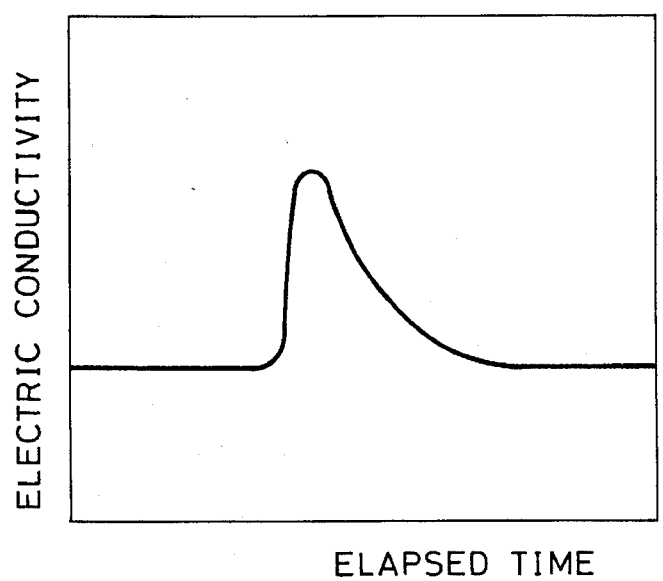

The relationship between the elapsed time from the introduction of chemical solution into sample pipe 13 and the electric conductivity of the chemical solution is shown in FIG. 2 as a graph.

Figure 3:
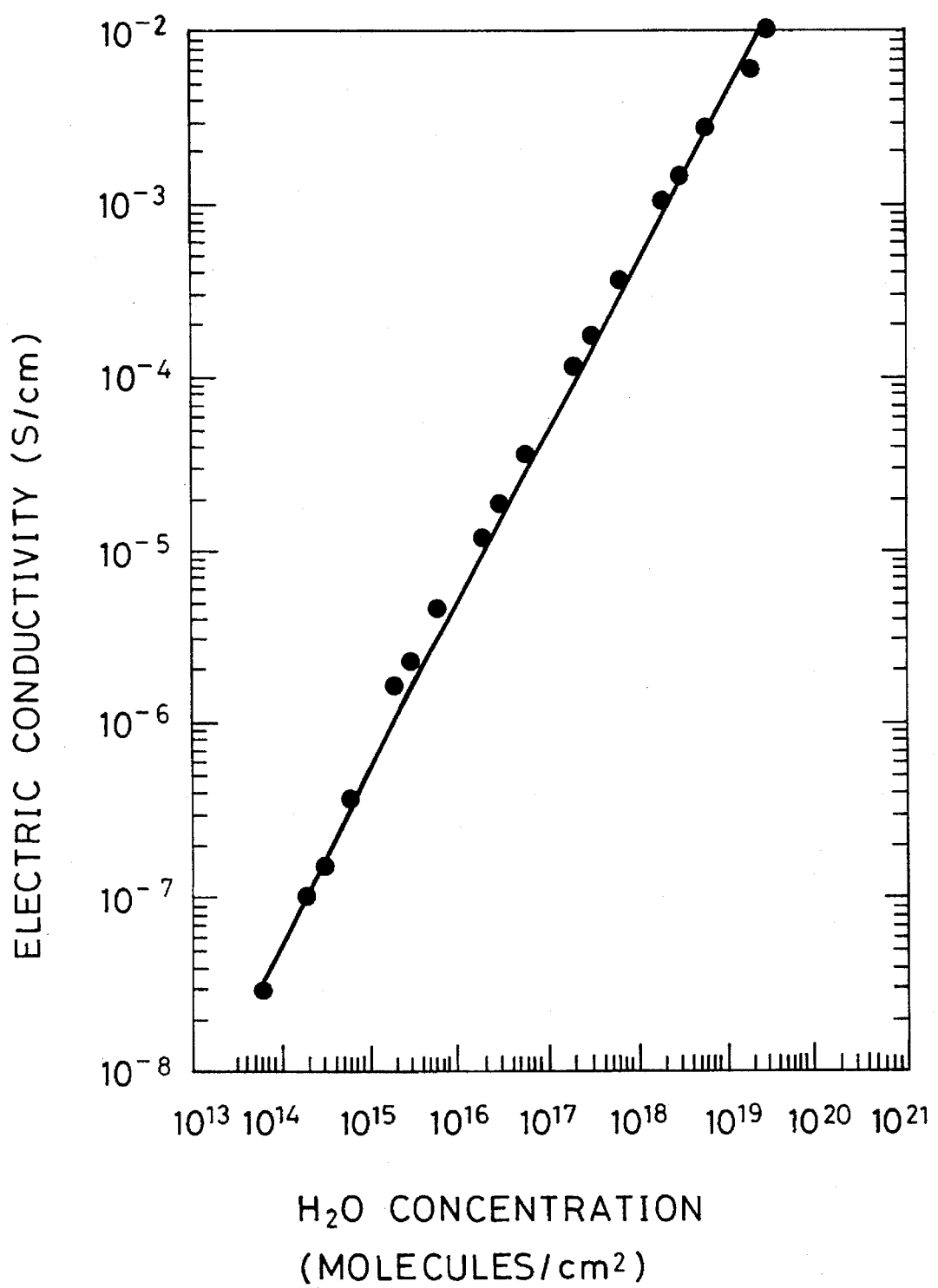

In other words, when the chemical solution which has dissolved the water content adsorbed by the surface of the sample pipe reaches conduction meter 3, the measured value of the electric conduction meter rises, and after this, declines until it reaches the electric conductivity of the original chemical solution. In the case in which anhydrous hydrogen fluoride is used as the chemical solution, the water content dissolved in the anhydrous hydrogen fluoride dissociates completely in the anhydrous hydrogen fluoride, so that the relationship between the electric conductivity as measured by the electric conduction meter and the water content is linear, as shown in FIG. 3. FIG. 3 shows the values when the temperature of the hydrogen fluoride is 0° C. Integrating the peak of FIG. 2, it is possible to obtain the number of adsorbed water molecules per unit surface adsorbed by the pipe from the relationship between the electric conductivity and water content of FIG. 3. The chemical solution possessing solubility with respect to water which is used in the present invention has high mutual interaction with water and mixes with water in any proportion; for example, anhydrous hydrogen fluoride is preferably used. It is possible to use industrial anhydrous hydrogen fluoride of approximately 6N as this anhydrous hydrogen fluoride; however, anhydrous hydrogen fluoride having a purity of 9N or more which is obtainable by the repeated refining, such as distillation or the like, of industrial anhydrous hydrogen fluoride, which has a water content of less than 40 ppb, and an electric conductivity of $1.0 \times 10^{-6}$ S/cm or less, is preferable for use in the measurement of very small amounts of water. By using anhydrous hydrogen fluoride of this purity, measurement of water content over a wide range from low concentrations to high concentrations becomes possible.

It is preferable that a stainless steel mass flow controller for liquids which is capable of the precise control of flow rates be used as the mechanism 2 for controlling the flow rate of the chemical solution. Furthermore, it is preferable that electric conduction meter 3 be capable of measuring electric conductivity within a range of $10^{-7}$–$10^{-2}$ S/cm, and in particular, a sealed-type inline-type electric conductivity meter which is capable of attachment to the piping is preferable.

The mechanism for supplying anhydrous hydrogen fluoride to the sample comprises a piping system connecting the anhydrous hydrogen fluoride storage vessel and the sample, and furthermore, the mechanism for sending anhydrous hydrogen fluoride from the sample to the electric conduction meter comprises a piping system connecting the sample and the electric conduction meter. These piping systems may employ various metals or alloys, since anhydrous hydrogen fluoride does not corrode metal. It is also possible to use Teflon or plastic; however, it is preferable that stainless steel be used which adsorbs little impurity gas, has high heat resistance, and an inner surface of which has been subjected to passivation treatment after being subjected to electrolytic polishing.

In the case in which anhydrous hydrogen fluoride is used as the chemical solution, because the boiling point of the anhydrous hydrogen fluoride is 19.5° C., it is desirable that the piping system, through which the hydrogen fluoride solution normally flows as a liquid, the flow rate control mechanism, and the electric conduction meter sensor cell be maintained at a temperature of 19.5° C. or less, and it is further desirable that these elements be maintained at a temperature of, for example, 0° C. Furthermore, the hydrogen fluoride which is discharged from the electric conduction meter 3 is recycled to a sealed vessel which is cooled to a temperature within a range of, for example, −10° C.—−30° C.

In the above, a measurement method for water content adsorbed by piping was discussed; however, by providing a sample room in place of the sample pipe of FIG. 1, and placing a sample within this room, it is possible to measure water content adsorbed not merely by piping, but by samples in various forms; for example, in the form of a powder or the like.

BRIEF DESCRIPTION OF THE DIAGRAMS

Figure 4:
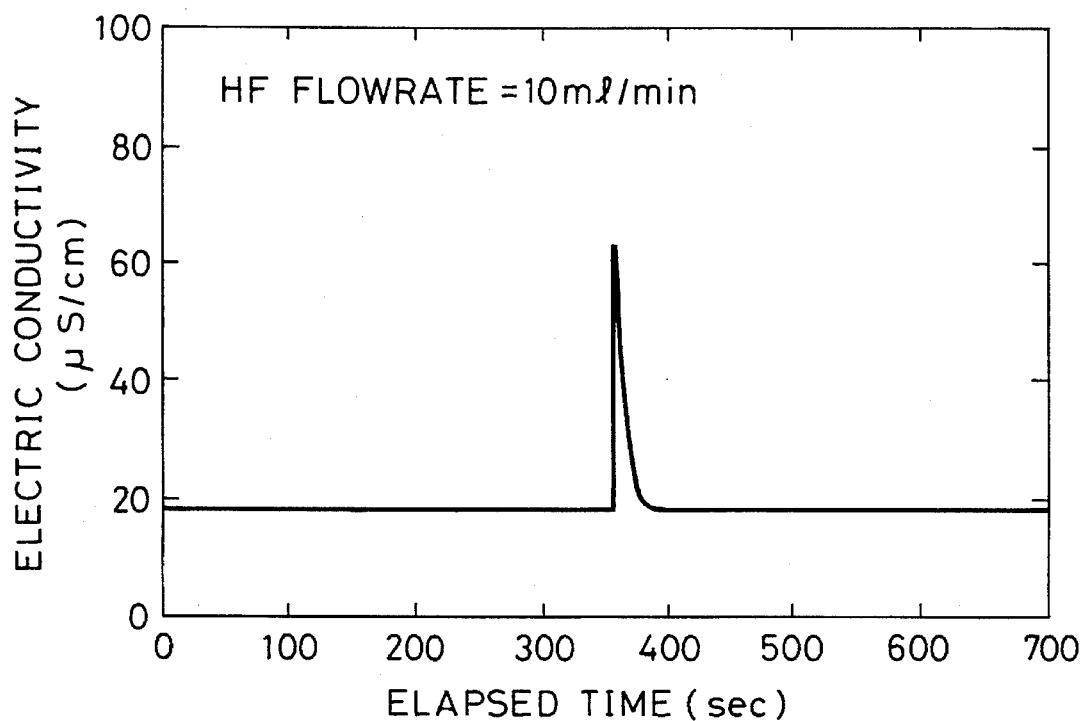
Figure 5:
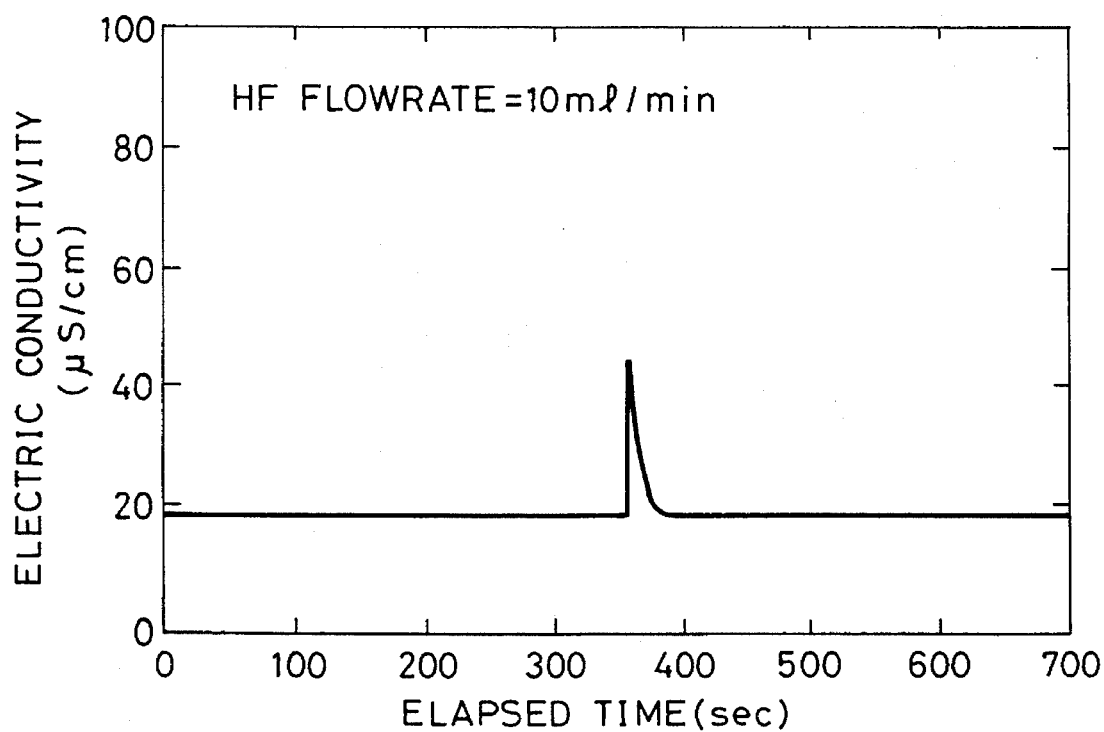

FIG. 1 is a conceptual diagram showing a structural example of a device for measuring water content in accordance with the present invention. FIG. 2 is a graph showing the variance over time of the electric conductivity of a chemical solution after the introduction of the chemical solution to a sample pipe. FIG. 3 is a graph showing the relationship between water concentration in hydrogen fluoride and electric conductivity. FIG. 4 is a graph showing the relationship between the elapsed time from the introduction of anhydrous hydrogen fluoride to the sample line of embodiment 1 (a stainless steel pipe subjected to oxide passivation processing and placed in an equilibrium adsorption state using Ar gas having a water content of 1000 ppb) and electric conductivity of the anhydrous hydrogen fluoride. FIG. 5 is a graph showing the relationship between the elapsed time from the introduction of anhydrous hydrogen fluoride to the sample line of embodiment 2 (a pipe subjected to electrolytic polishing and having $SiO_2$ formed on the inner surface thereof) and electric conductivity of the anhydrous hydrogen fluoride.

Explanation of the References 1 chemical solution storage vessel, 2 flow rate control mechanism, 3 electric conduction meter, 4, 5, 6, 7, 8, 9, 10, 11 valves, 12 reference line, 13 sample line.

BEST MODE FOR THE EXECUTION OF THE INVENTION

Hereinbelow, the present invention will be explained based on embodiments.

Embodiment 1

Ar gas having the water content concentrations shown in Table 1 was introduced at a temperature of 25° C. into stainless steel pipes having a diameter of ¼ inches and a length of 4m, which had been subjected to various surface treatments, and after an equilibrium adsorption state was reached, the water content adsorbed by the inner surface of the stainless steel pipe was measured. In these measurements, anhydrous hydrogen fluoride having an electric conductivity of 18 micro S/cm was used as the chemical solution. An example of measurement results obtained with respect to the change over time in electric conductivity of the anhydrous hydrogen fluoride is shown in FIG. 4, and furthermore, the adsorbed water contents obtained with respect to various pipes are shown in Table 1.

TABLE 1

| Water Content Concentration in the Ar Gas | Adsorbed Water Content (molecule/cm$^2$) | | |
|---|---|---|---|
| (ppb) | BA | EP | OP |
| 140 | $9 \times 10^{13}$ | $7 \times 10^{13}$ | $20 \times 10^{13}$ |
| 1000 | $15 \times 10^{13}$ | $15 \times 10^{13}$ | $36 \times 10^{13}$ |

BA: pipe subjected to brightening annealing, EP: pipe subjected to electrolytic polishing, OP: pipe subjected to oxide passivation processing.

The above results Showed good agreement with results measured by means of the APIMS method.

Embodiment 2

Sample stainless steel tubes which had been subjected to electrolytic polishing treatment were produced having formed, on the inner surface thereof, a Si film, a $SiO_2$ film, a film (Si—H) formed by the termination of dangling bonds by means of hydrogen after Si film formation, and a film (Si—F) formed by the termination of dangling bonds by means of fluorine after Si film formation, and Ar gas having a water content of 100 ppb was introduced into the sample pipes at a temperature of 25° C., and after the achievement of and equilibrium adsorption state, the water content adsorbed by the inner surface was measured in a manner identical to that of embodiment 1. An example of the measurement results obtained with respect to the change over time in the electric conductivity of the anhydrous hydrogen fluoride is shown in FIG. 5, and furthermore, the adsorbed water content obtained with respect to various pipes is shown in Table 2.

TABLE 2

| Type of Membrane Formed on the Inner Surface of the Pipe | Adsorbed Water Content (molecules/cm$^2$) |
|---|---|
| Si | $3 \times 10^{13}$ |
| $SiO_2$ | $20 \times 10^{13}$ |
| Si—H | $1.5 \times 10^{13}$ |
| Si—F | $32 \times 10^{13}$ |

The results of Table 2 showed good agreement with the measurement results obtained by means of the APIMS method.

The measurement of the adsorbed water content in the above embodiments was completed in less than 15 minutes per sample, so that; the measurement period, which conventionally required a number of hours, was greatly reduced.

INDUSTRIAL APPLICABILITY

By means of the present invention, it is possible to provide a method and a device for measuring water content which is capable of measuring water content adsorbed by various samples with a high degree of precision and in a short period of time.

We claim:

1. A method for measuring the water content of a sample, the method comprising the steps of:

measuring the electrical conductivity of an anhydrous hydrogen fluoride solution which has not contacted a sample;

contacting a sample with said solution to adsorb water absorbed by the said sample;

measuring the electrical conductivity of said solution after said solution has contacted said sample; and determining the water content of the sample by correlating the measured electrical conductivity of the solution which has contacted the sample and the measured electrical conductivity of the solution which has not contacted the sample.

2. An apparatus for measuring the water content of a sample comprising:

a vessel containing an anhydrous hydrogen fluoride solution;

containment means for containing a sample;

means for measuring the electrical conductivity of said solution;

means for supplying said solution at a controlled rate from said vessel to said measuring means;

means for supplying said solution at a controlled rate from said vessel to said containment means for contacting said sample; and means for supplying solution which has contacted said sample from said containment means to said measuring means.

* * * * *

UNITED STATES PATENT AND TRADEMARK OFFICE
CERTIFICATE OF CORRECTION

PATENT NO. : 5,504,009
DATED : April 2, 1996
INVENTOR(S) : Tadahiro Ohmi et al

It is certified that error appears in the above-indentified patent and that said Letters Patent is hereby corrected as shown below:

```
On the title  page of the patent add:

--[22]   PCT filed:        July 16, 1992

[86]   PCT No.:          PCT/JP92/00912
            §371 Date:        Jan. 14, 1994
            §102 (e) Date:    Jan. 14, 1994

[87]   PCT Pub. No.:     WO 93/02351
            PCT Pub. Date:    Feb. 4, 1993--
```

Signed and Sealed this

Twentieth Day of August, 1996

Attest:

BRUCE LEHMAN

*Attesting Officer*        *Commissioner of Patents and Trademarks*